US012788347B2

(12) United States Patent
O'Connor et al.

(10) Patent No.: US 12,788,347 B2
(45) Date of Patent: Nov. 10, 2026

(54) SYSTEMS AND METHODS FOR LESION DEPTH DETERMINATION IN MOLECULAR BREAST IMAGING

(71) Applicants: Mayo Foundation for Medical Education and Research, Rochester, MN (US); CMR Naviscan, Carlsbad, CA (US)

(72) Inventors: Michael K. O'Connor, Rochester, MN (US); Weidong Luo, Carlsbad, CA (US)

(73) Assignees: Mayo Foundation for Medical Education and Research, Rochester, MN (US); CMR Nayiscan, Carlsbad, CA (US)

( * ) Notice: Subject to any disclaimer, the term of this patent is extended or adjusted under 35 U.S.C. 154(b) by 207 days.

(21) Appl. No.: 18/716,029

(22) PCT Filed: Dec. 5, 2022

(86) PCT No.: PCT/US2022/080917
§ 371 (c)(1),
(2) Date: Jun. 3, 2024

(87) PCT Pub. No.: WO2023/102564
PCT Pub. Date: Jun. 8, 2023

(65) Prior Publication Data

US 2025/0032075 A1 Jan. 30, 2025

Related U.S. Application Data

(60) Provisional application No. 63/285,704, filed on Dec. 3, 2021.

(51) Int. Cl.
*A61B 6/00* (2024.01)
*A61B 6/12* (2006.01)
(Continued)

(52) U.S. Cl.
CPC ................ *A61B 6/502* (2013.01); *A61B 6/12* (2013.01); *A61B 6/4258* (2013.01)

(58) Field of Classification Search
CPC ......... A61B 6/502; A61B 6/12; A61B 6/4258; A61B 6/0414
See application file for complete search history.

(56) References Cited

U.S. PATENT DOCUMENTS 8,071,949 B2 12/2011 Majewski et al.
8,923,952 B2 12/2014 O'Connor et al.
(Continued)

OTHER PUBLICATIONS

Deepu, R. et al., A Mathematical Model for the Determination of Distance of an Object in a 2D Image, In Proceedings of the International Conference on Image Processing, Computer Vision, and Pattern Recognition (IPCV), 2013, 5 pages.
(Continued)

*Primary Examiner* — Joel Lamprecht
(74) *Attorney, Agent, or Firm* — Quarles & Brady LLP

(57) ABSTRACT

Systems and methods are provided for lesion depth determination in molecular breast imaging. The depth of a lesion in a breast of a subject may be determined during a molecular breast imaging ("MBI") procedure where the resolving power of the detectors, such as gamma cameras, that degrades with distance from the face of the detector is exploited. By comparing the apparent size of a lesion in two opposing detectors, it is possible to estimate the distance of the lesion from each detector by modeling or measuring the resolution that changes with distance from the detectors. The systems and methods may be used during biopsy procedures to indicate the appropriate needle depth for biopsy of the lesion.

17 Claims, 6 Drawing Sheets

(51) Int. Cl.
*A61B 6/42* (2024.01)
*A61B 6/50* (2024.01)

(56) References Cited

U.S. PATENT DOCUMENTS

2010/0104505 A1* 4/2010 O'Connor ............ A61B 6/0414 600/431
2011/0268339 A1* 11/2011 Volokh .................. G06T 7/0012 382/132

OTHER PUBLICATIONS

Judy, P. et al., Molecular Breast Imaging with Directly Opposing Compact Gamma Cameras, IEEE Nuclear Science Symposium Conference Record, 2007, M20-1, pp. 4040-4043.
Welch, B. et al., Gamma-Guided Stereotactic Breast Biopsy System, IEEE Transactions on Nuclear Science, 2006, 53(5):2690-2697.
PCT International Search Report and Written Opinion, PCT/US2022/080917, Mar. 15, 2023, 15 pages.

* cited by examiner

SYSTEMS AND METHODS FOR LESION DEPTH DETERMINATION IN MOLECULAR BREAST IMAGING

BACKGROUND

Breast cancer screening has been recommended for many decades, particularly in women over the age of fifty. The combination of early detection and improved therapy in the U.S. has resulted in a significant reduction in breast cancer mortality, with similar reductions being observed in other countries. Despite the success of screening mammography, however, it is also recognized that mammography is a less than perfect screening method. The limitations of mammography are particularly evident in women with mammographically dense breasts. It has been shown that the sensitivity of mammography decreases with increasing mammographic density, and is less than fifty percent for women with an extremely dense breast pattern on a mammogram.

The reduced sensitivity of mammography with increasing mammographic density is compounded by the fact that increased density is a significant risk factor for breast cancer. Given that a dense breast pattern occurs more frequently in younger women, this factor significantly diminishes the value of mammography in the screening of young women who have a high familial risk of breast cancer.

A second major limitation to screening mammography is in the evaluation of women at high risk of breast cancer. Numerous studies have demonstrated that in women with a high genetic risk of breast cancer, mammography has a sensitivity of between 33-43 percent. Most of these studies have been performed in women with an average age of forty, so part of the explanation for the poor performance of mammography in these studies may be due to the presence of dense breast patterns in a significant percentage of the mammographic images.

A possible solution to the problem of the detection of breast lesions in dense breast tissue is to use ultrasound in such patients. Ultrasound is attractive for supplemental screening because it is widely available, is well-tolerated by patients, and involves no radiation. However, while supplemental ultrasound screening uncovers more breast cancers, it also substantially increases the risk of a false positive cancer finding and unnecessary biopsy. Hence, the use of whole-breast ultrasound as a sole identifier of breast malignancies is questionable. Even in combination with mammography, the two anatomical techniques have significant limitations. It would be of considerable benefit to provide a complementary method that provides functional information about lesions seen on ultrasound. Such a method would significantly reduce the number of false positive cases, and allow the radiologist to evaluate those lesions that demonstrate both a functional and anatomical abnormality.

Over the last several years, a number of nuclear medicine-based technologies have been developed that have application in breast imaging. Included in these are positron emission mammography ("PEM") and molecular breast imaging ("MBI"). In PEM the breast is compressed between two opposing detectors and the 511 keV gamma rays emitted by a positron emitting radiopharmaceutical, such as F-18 fluoro-deoxyglucose, are detected by coincidence imaging between the two opposing detectors. The PEM images provide an image of glucose utilization by breast tissue and have been shown to be capable of detecting small cancers in the breast. Unlike anatomical techniques such as mammography and ultrasound, PEM is not influenced by dense breast tissue.

The second nuclear medicine-based technique is MBI. This technology employs one or two small gamma cameras. The breast is compressed between a camera and a compression paddle, or between two gamma cameras, and radiation emitted by single-photon radiopharmaceutical(s) (for example, Tc-99m sestamibi) is detected after collimation. MBI is a planar imaging technique without tomographic capability. The MBI system has been shown to have a very high sensitivity, for example in some cases greater than ninety percent, for the detection of lesions smaller than ten millimeters. In addition, it has been found that, in some cases, MBI can detect three times as many cancers as digital and analog mammography in asymptomatic women at increased risk of breast cancer.

Beyond sensitivity differences, technologies that provide functional images of the breast, such as MBI, can detect lesions not visible with conventional mammography. However, MBI conventionally lacks a simple, integrated system for determining lesion depth information. It would therefore be desirable to provide an MBI system that can provide for more accurate depth determination for a lesion that does not rely upon a separate imaging system, such as ultrasound. Additionally, it would be desirable to provide an MBI system that would also allow for more accurate breast biopsy guidance.

SUMMARY OF THE DISCLOSURE

The present disclosure addresses the aforementioned drawbacks by providing, in one configuration, an MBI system that includes a first detector head and a second detector head that are operably coupled to the MBI system. The first detector head includes a first gamma ray detector having a first system resolution, and the second detector head includes a second gamma ray detector having a second system resolution. The first and second detector heads are moveable relative to each other to provide a compression therebetween. The MBI system also includes a processor in communication with the first detector head and the second detector head. The processor is configured to: determine the first system resolution of the first gamma ray detector as a function of depth from a facing surface of the first gamma ray detector; determine the second system resolution of the second gamma ray detector as a function of depth from a facing surface of the second gamma ray detector; determine a distance between the first detector head and the second detector head; and, when a breast is arranged between the first detector head and the second detector head, determine a depth for a lesion in the breast based on the first system resolution, the second system resolution, and the distance between the first and second detector heads.

In another configuration, a method is provided for determining a depth of a lesion in a breast using an MBI system. The method includes acquiring a first image of the breast using a first gamma ray detector in a first detector head assembly of the MBI system, and a second image of the breast using a second gamma ray detector in a second detector head assembly of the MBI system. A first system resolution of the MBI system as a function of depth in the breast relative to the first gamma ray detector, and a second system resolution of the MBI system as a function of depth in the breast relative to the second gamma ray detector are both determined using a computer system. A distance between the first detector head and the second detector head when the first and second images were acquired is also determined using the computer system. Then, a depth for the lesion in the breast is determined, using the computer system, based on the first system resolution, second system resolution, and the distance between the first and second detector heads.

DETAILED DESCRIPTION

Systems and methods are provided for lesion depth determination in molecular breast imaging. In a non-limiting example, the depth of a lesion in a breast of a subject may be determined during a molecular breast imaging procedure. The systems and methods exploit how the resolving power of the detectors, such as gamma cameras, used in molecular breast imaging degrade with distance from the face of the detector. By comparing the apparent size of a lesion on the two opposing detectors, it is possible to estimate the distance of the lesion from each detector. The systems and methods may be used during molecular breast imaging-guided biopsy to indicate the appropriate needle depth for biopsy of the lesion.

Figure 1:
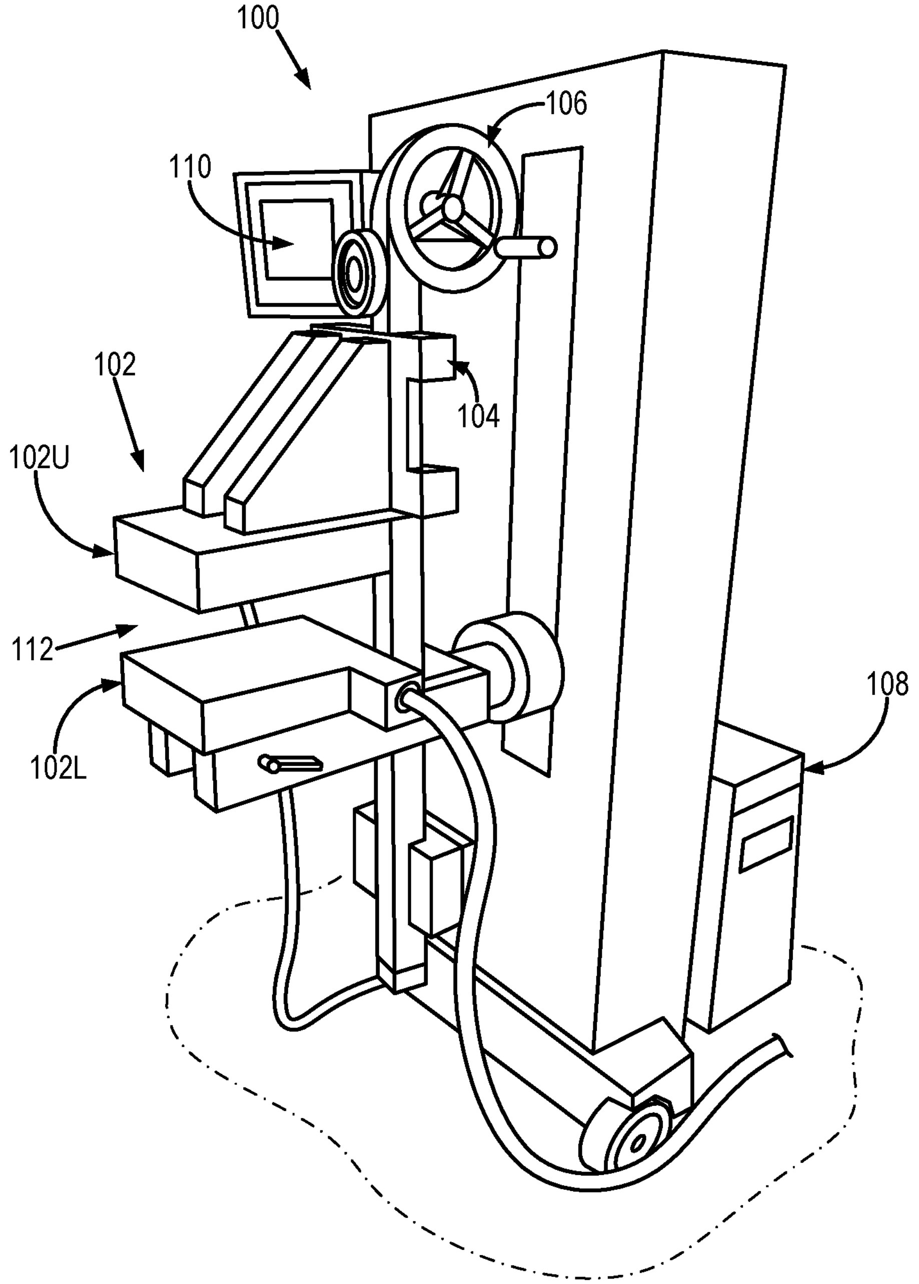
FIG. 1 is an illustration of an example molecular breast imaging ("MBI") system that can be implemented in some embodiments described in the present disclosure.

Referring to FIG. 1, a molecular breast imaging ("MBI") system 100 includes two opposing radiation detectors, shown as detector heads 102. In some embodiments, the radiation detectors may be cadmium zinc telluride ("CZT") detectors, or the like. In particular, the detector heads 102 include an upper detector head 102U and a lower detector head 102L. Examples of MBI systems and methods for their use are described, for example, in U.S. Pat. No. 8,923,952, which is herein incorporated by reference in its entirety. Each detector head 102U, 102L may be, for example, 20-24 cm by 16-20 cm in size and mounted on a modified upright type mammographic gantry 104. In one configuration, the detector heads 102 are LumaGEM® solid-state cameras (CMR Naviscan, Inc.; Carlsbad, California) having a pixel size of 1.6 mm.

The relative position of the detector heads 102 can be adjusted using a user control 106. Specifically, the detector head assemblies 102 are, preferably, designed to serve as a compression mechanism. Accordingly, this system configuration reduces the maximum distance between any lesion in the breast and either detector head 102 to one-half of the total breast thickness, potentially increasing detection of small lesions without additional imaging time or dose. The MBI system 100 includes a processor 108 for processing the signals acquired by the detector heads 102 to produce an image, which may be displayed on an associated display 110.

In general, the detector heads 102U, 102L are arranged so as to form an examination region 112 there between. The examination region 112 is defined with respect to a first imaging plane and a second imaging plane. The first imaging plane is defined, for example, by the extension of the upper detector head 102U along the examination region 112, and the second imaging plane is defined, for example, by the extension of the lower detector head 102L along the examination region 112.

One of the detector heads 102 of an MBI system can be configured to provide an MBI system amenable to combined MBI and ultrasound imaging, or combined MBI and breast biopsy. In other configurations, one of the detector heads 102 can be replaced with an ultrasound probe or a whole-breast ultrasound imaging apparatus particularly configured for use with the MBI system. In general, configurations of an MBI system that are amenable for combined MBI and ultrasound imaging, or combined MBI and breast biopsy, include detector heads 102 that can be moved relative to one another such that the breast becomes accessible for an ultrasound imaging system or biopsy device. Thus, in general, the MBI system may include a first detector head that is configured to move between a first position and a second position relative to a second detector head. Generally, such a first position would be one in which the two detector heads are opposed and configured for MBI, and such a second position would be one in which the two detector heads are no longer opposed, thereby providing access to the breast for ultrasonic imaging or biopsy. For example, the upper detector head 102U may be configured to rotate away from the lower detector head 102L, or, the detector heads 102 may be configured to move longitudinally relative to one another.

The detector head 102 may include a gamma ray detector, a collimator, and an inner collimator frame. The gamma ray detector and collimator may be arranged such that the collimator is substantially parallel to the imaging plane defined by the detector head 102. The detector head may include a compression plate. By way of example, the detector array may be composed of CZT detector elements. The compression plate may provide a contact surface for receiving and compressing a portion of a subject under examination, such as a portion of the subject's breast.

Current MBI gantry designs work adequately for conventional breast imaging, but do not easily provide an accurate determination of the depth of a lesion, or thereby provide accurate guidance for a biopsy device. Thus, the provided MBI systems and methods are configured to provide accurate determinations of a depth of a lesion, such as a lesion located in the subject's breast, and thereby may provide guidance for a biopsy of the lesion.

Resolution degrades as an object is moved away from the collimator face of an MBI imaging system. This may manifest as a blurring of the object as depicted in the image. Conventionally to compensate for this degradation in resolution, considerable effort is put into keeping the gamma camera as close to the body as possible during an imaging study. This form of compensation places breast tissue in close contact with the collimator face for breast imaging applications.

Collimator resolution may be determined by:

$$\text{Resolution} = \text{hole diameter} * \frac{\text{hole length} + \text{distance from collimator face}}{\text{hole length}}. \tag{1}$$

A notable feature of this equation is that resolution is linearly dependent upon distance. For a point source, the apparent size is given by its full width at half maximum ("FHWM"). For a larger object, the apparent size is a convolution of the true object size and system resolution. For an object at distance D from the collimator face, the apparent size is given by:

$$\text{Apparent size}^2 = \text{True size}^2 + \text{System Resolution at } D^2. \tag{2}$$

Figure 2:
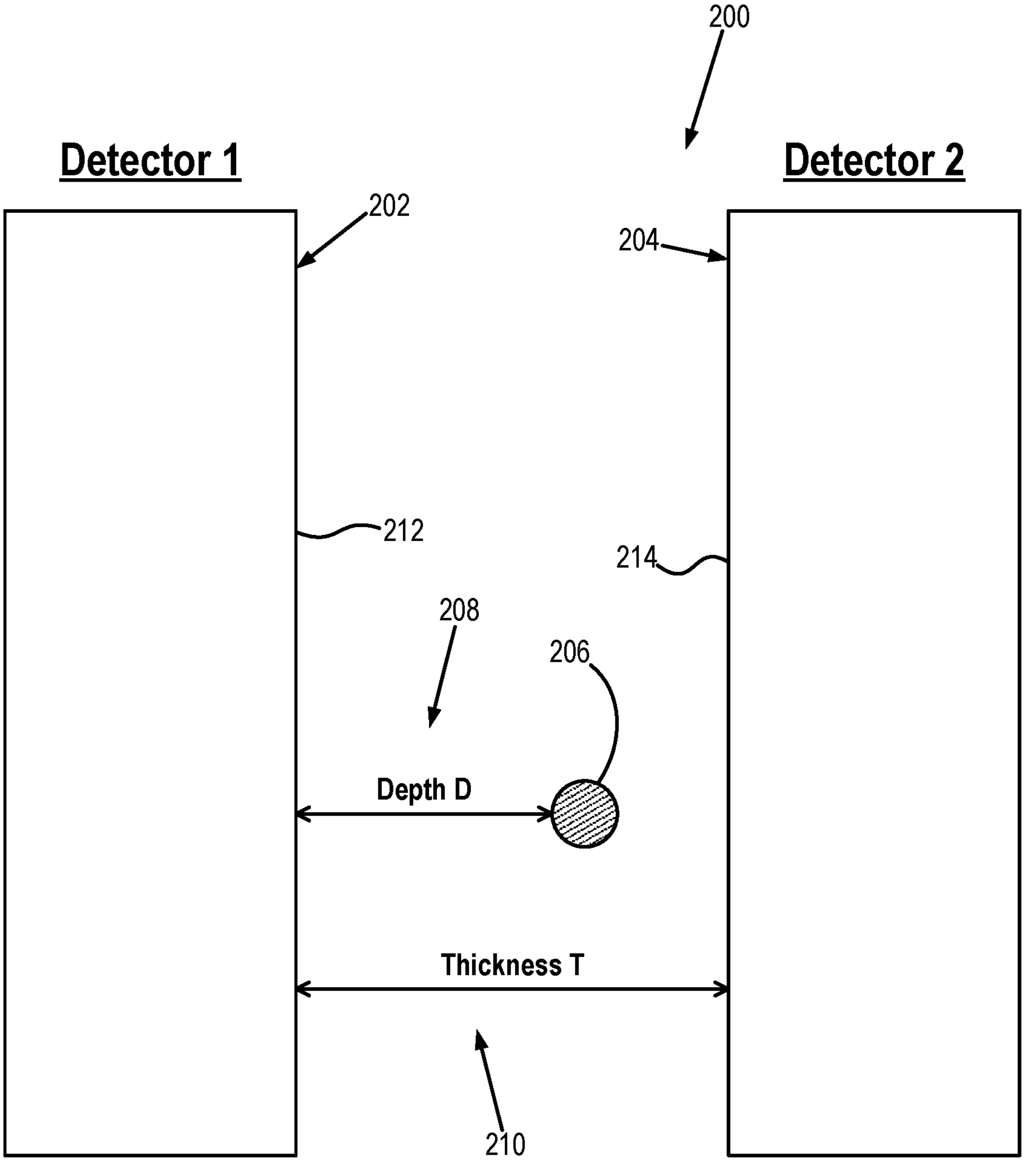
FIG. 2 is an illustration of a non-limiting example dual-detector MBI system with two identical detectors.

Referring to FIG. 2, a non-limiting example dual-detector MBI system 200 having a first detector 202 and a second detector 204 (which may be identical detectors) is shown. The apparent size of a lesion 206 will depend upon its distance 208 from each detector. The distance between the detectors 202 and 204 is given by thickness 210. The apparent size of the lesion 206 may be determined by the following equations.

$$AS_1^2 = TS_1^2 + SR(D)^2; \tag{3}$$

$$AS_2^2 = TS_2^2 + SR(T-D)^2; \tag{4}$$

where $AS_1$ and $AS_2$ are the apparent size of the lesion for the first and second detectors, respectively; $TS_1$ and $TS_2$ are the true size of the lesion for the first and second detectors, respectively; SR(D) is the system resolution at distance D; and SR(T−D) is the system resolution at distance T−D.

Subtracting Eqns. (3) and (4), the follow expression may be found:

$$AS_1^2 - AS_2^2 = SR(D)^2 - SR(T-D)^2. \tag{5}$$

The expression of Eqn. (5) is no longer dependent on knowledge of true lesion size. The FWHM measurements of a lesion may be used provide the apparent lesion size for the first detector 202 and the second detector 204. In a non-limiting example, the thickness 210 may be a breast thickness, T, which may be recorded as the distance between the opposing collimator faces (e.g., actual breast thickness plus any additional thickness associated with compression paddles, etc.). The Eqn. (5) may be solved for depth, D, if it is known how the system resolution varies with depth.

Figure 3:
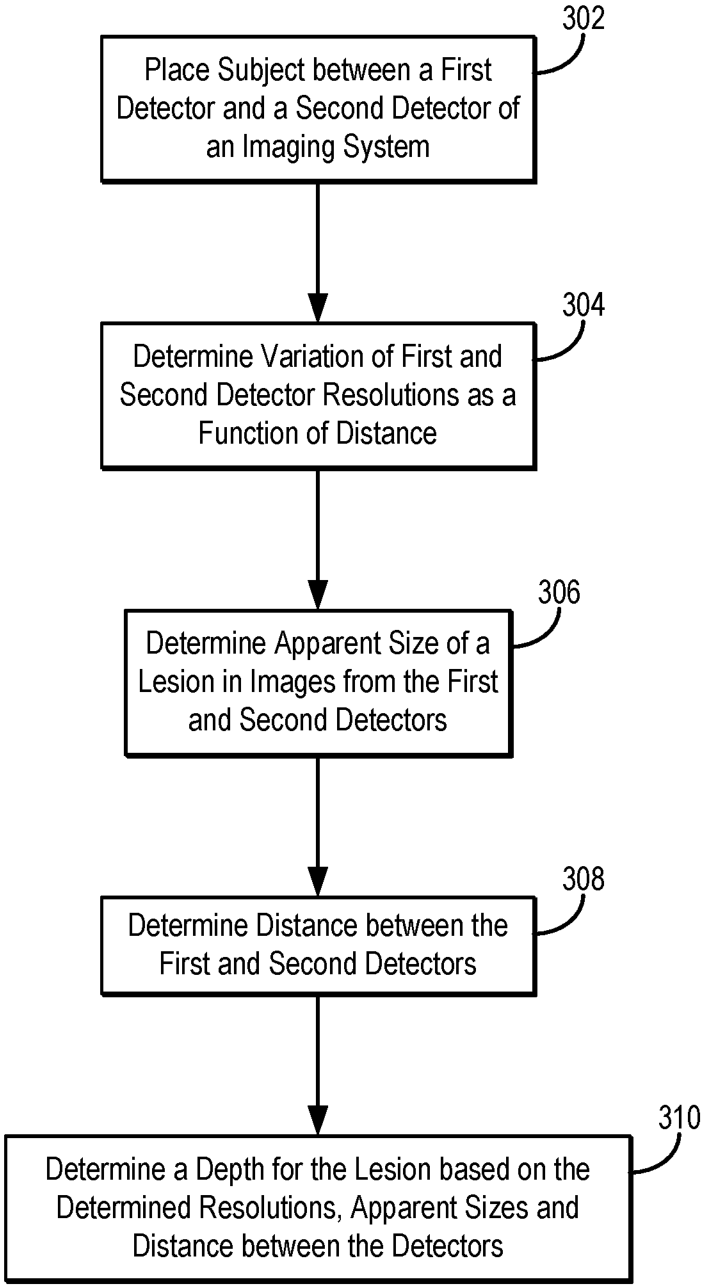
FIG. 3 is a flowchart of non-limiting example steps for determining the depth of a lesion in a subject.

Referring to FIG. 3, a flowchart of non-limiting example steps for determining a depth for a lesion in a subject is shown. A subject or a portion of a subject may be placed between a first detector and a second detector of an imaging system at step 302. In non-limiting examples, the portion of the subject may be a breast, and the imaging system may be an MBI system. Images are then acquired using the imaging system. For example, a first image can be obtained using the first detector of an MBI system and a second image can be obtained using the second detector of the MBI system.

The variation of the resolution of the first and second detectors as a function of distance, or depth, may then be determined at step 304. The resolution variation can be determined as a function of distance from a facing surface of the respective detector (i.e., the depth). For instance, with reference again to FIG. 2, the depth, D, relative to the first detector 202 can be measured as the distance from the facing surface 212 of the first detector 202 (i.e., the surface facing towards the second detector 204), and the depth relative to the second detector 204 can be measured as the distance from the facing surface 214 of the second detector (i.e., the surface facing towards the first detector 202).

The apparent size of a lesion in images from the first and second detectors may also be determined at step 306. The distance between the first and second detectors may also be determined at step 308. The depth of the lesion in the portion of the subject can then be determined at step 310 based on the determined resolutions of the first and second detectors, the apparent sizes of the lesion in the images, and the distance between the detectors of the MBI system. In non-limiting examples, the lesion is a breast lesion or a breast tumor and the breast is compressed between the first and second detectors of a MBI system.

Using data over a range of depths, system resolution may be given by a linear model of measured system resolution over the range of depths. In some configurations, the linear model of system resolution may be represented by Eqn. (6) below. In a non-limiting example, a range of depths may include 3-9 cm, as shown in Eqn. (7) below for an example MBI system. An appropriate range of depth values for clinical studies may be used.

$$SR(d) = d \cdot a + b; \tag{6}$$

where "a" represents the slope of the linear model fit to the system resolution over the range of depths, and "b" represents the intercept for the linear model. In some configurations, these parameters are collimator dependent, and may be reassessed for different collimator designs.

$$SR[\text{cm}] = d[\text{cm}] \cdot 0.1524 + 0.321. \tag{7}$$

In the non-limiting example of Eqn. (7), the form of Eqn. (6) was used with a range of depths that included 3-9 cm to determine the system resolution of an example MBI system. The system resolution may be determined for a detector by determining the resolution over a defined or measured range of depths and fitting a model, such as a linear model of the form of Eqn. (6), to the detector response over the range of depths. The model may then allow for the system resolution at depths outside of the measured range of depths to be determined, for instance, using:

$$\begin{aligned} AS_1^2 - AS_2^2 &= SR(D)^2 - SR(T-D)^2 \\ &= (aD+b)^2 - (a(T-D)+b)^2 \\ &= -2abT - a^2T^2 + 2a^2TD + 4abD \end{aligned}; \tag{8}$$

where a and b are the slope and intercept of a linear model as described above, and T represents the thickness or distance between the first and second detectors. Since a, b, and T are known, and the FWHM for the first and second detectors are measurable since $AS_1$ and $AS_2$ are the apparent size of the lesion for the first and second detectors, which can be equated to the FWHM, a solution for the lesion depth, D, yields:

$$D = \frac{FWHM_1^2 - FWHM_2^2 + 2abT + a^2T^2}{2a^2T + 4ab}; \quad (9)$$

where $FWHM_1$ and $FWHM_2$ are the FWHM for the first and second detector, respectively.

In a non-limiting example, the systems and methods of the present disclosure may be configured for implementation in a biopsy system, which may use the depth determination for guiding a biopsy of a lesion. The values for the slope and intercept parameters (i.e., a and b) may be precalculated and stored in a parameter file for use by the system. The system may also be configured to contain precalculated the values for $FWHM_1$ and $FWHM_2$, and may be configured for determining breast thickness T.

Referring to FIGS. 4-7, non-limiting example simulation results are shown. In example studies, simulations were run to compare actual lesion depth with calculated lesion depth as a function of lesion size. The results showed good accuracy for lesions 13 mm and smaller.

Figure 4A:
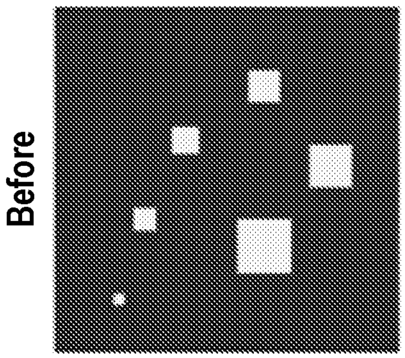
FIG. 4A is a non-limiting example image depicting lesions in a phantom.
Figure 4B:
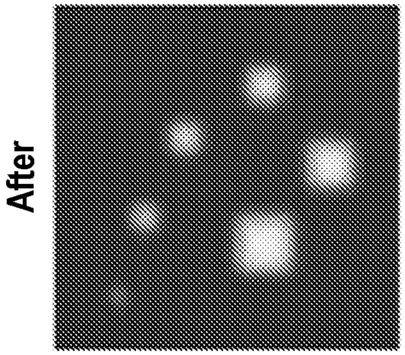
FIG. 4B is a non-limiting example simulated image of the lesions depicted in FIG. 4A for an upper detector of an MBI system.
Figure 5:
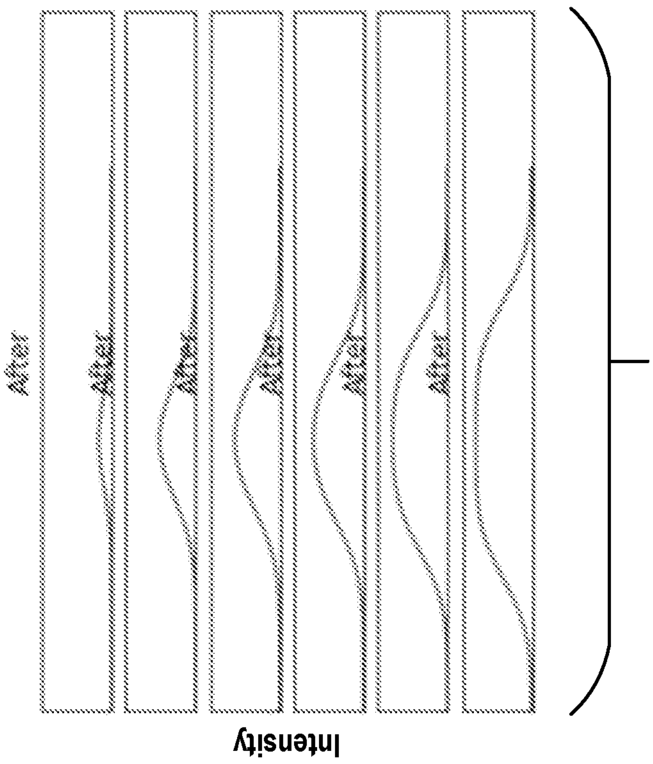
FIG. 5 is a graph of line profiles for the lesions shown in FIGS. 4A and 4B.

Referring to FIG. 4A, an image depicting lesions in a phantom is shown. Referring to FIG. 4B, a simulated image of the lesions depicted in FIG. 4A is shown for an upper detector at a depth of 20 mm. Referring to FIG. 5, line profiles for the lesions shown in FIGS. 4A and 4B are shown for the non-limiting example simulated image data for an upper detector at a depth of 20 mm.

Figure 6A:
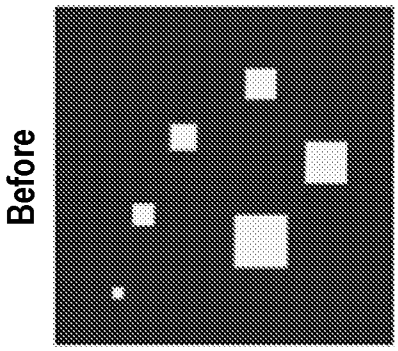
FIG. 6A is a non-limiting example image depicting lesions in a phantom.
Figure 6B:
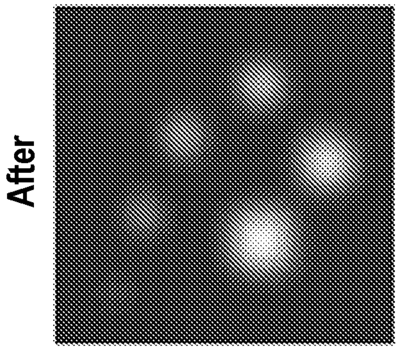
FIG. 6B is a non-limiting example simulated image of the lesions depicted in FIG. 6A for a lower detector of an MBI system.
Figure 7:
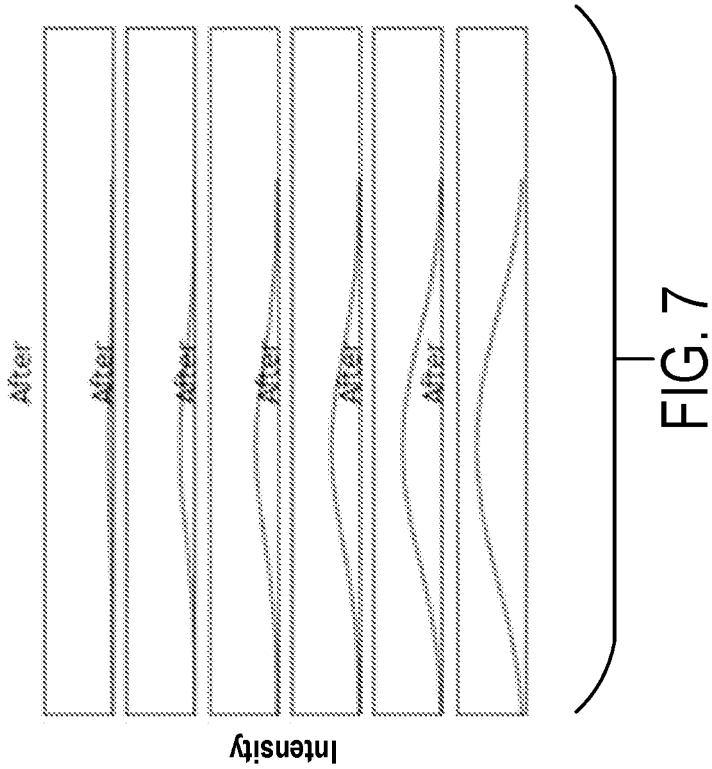
FIG. 7 is a graph of line profiles for the lesions shown in FIGS. 6A and 6B.

Referring to FIG. 6A, an image depicting lesions in a phantom is shown. Referring to FIG. 6B, a simulated image of the lesions depicted in FIG. 4A is shown for a lower detector at a depth of 20 mm. Referring to FIG. 7, line profiles for the lesions shown in FIGS. 6A and 6B are shown for the non-limiting example simulated image data for a lower detector at a depth of 20 mm. Table 1 provides a summary of the simulation results.

TABLE 1

Simulation Summary of Depth Calculation

| | Depth (mm) | | | | | |
|---|---|---|---|---|---|---|
| | 5 × 5 mm | 9 × 9 mm | 11 × 11 mm | 13 × 13 mm | 17 × 17 mm | 21 × 21 mm |
| Actual | 20 | 20 | 20 | 20 | 20 | 20 |
| Calculated | 20.04 | 20.42 | 21.02 | 21.86 | 24.18 | 26.51 |

Using line sources, the system resolution may be measured as a function of depth for an MBI system. The water tank was 20 cm in width and the line sources were attached to a weighted vertical acrylic plate that can be positioned at various depths in the tank. Sources were orientated at 45 degrees and 30 degrees to prevent aliasing with the square collimator hole patterns. Measurements were made with the line sources at depths ranging from 2-18 cm.

Figure 8:
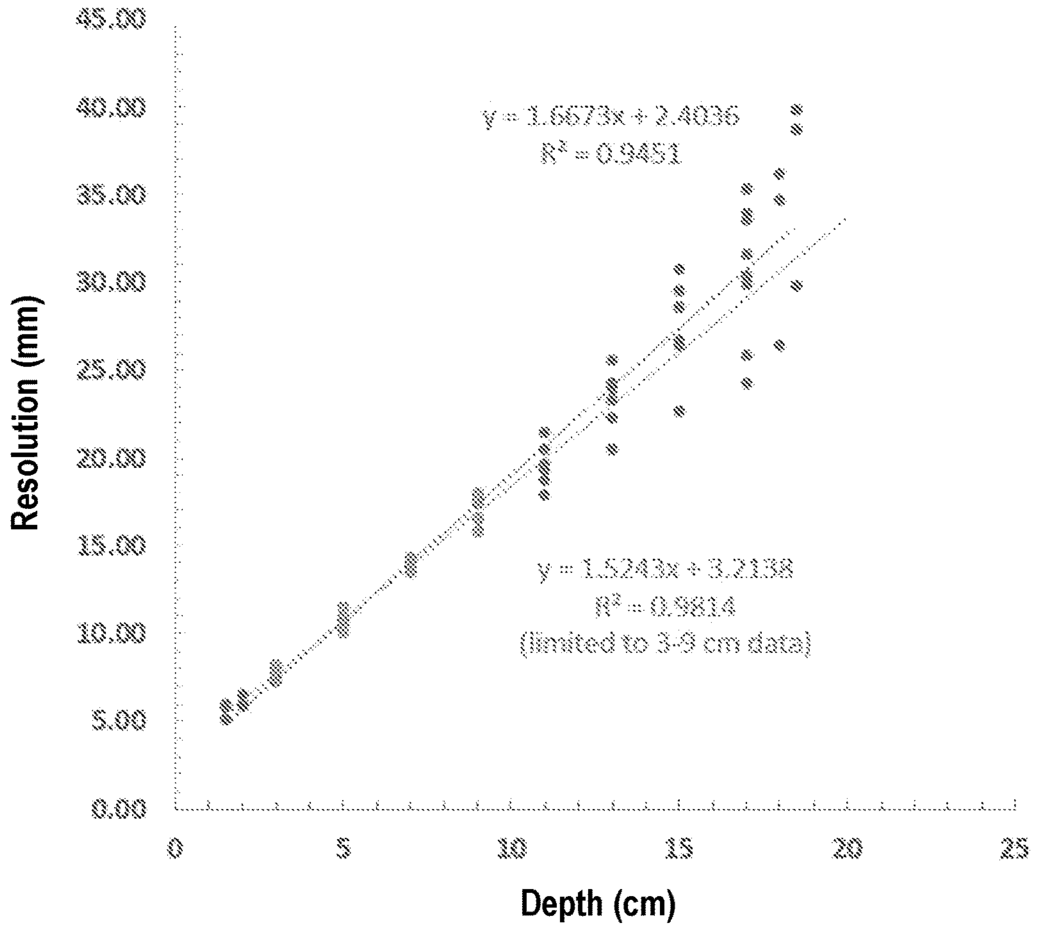
FIG. 8 is a graph of the relationship between system resolution and depth for a non-limiting example MBI system.

Referring to FIG. 8, the relationship between system resolution and depth for the non-limiting example MBI system is shown in a graph. Different linear approximations may be used to model the variation in resolution at different depths, as shown, where a first linear model is used below 3 cm in depth, a second linear model is used for depths ranging from 3-9 cm, and a third linear model is shown for depths above 9 cm. Any number of models may be used to model the resolution of a detector with depth. A non-linear model or any number of non-linear models may also be used to model the resolution of a detector.

In some configurations, the systems and methods of the present disclosure may be incorporated into a graphical user interface ("GUI") showing depth estimates along with any other estimates of depth. A GUI may provide for a user to quickly identify the depth of a lesion and what resolution may be expected at that depth. The GUI may also be used as a quality control confirmation with depth compared to phantom study data.

In some configurations, thicker breasts where there is a large difference in apparent lesion size may provide for higher accuracy in depth determination. Small lesions in the 5-10 mm range may also have depth determined with greater accuracy.

Figure 9:
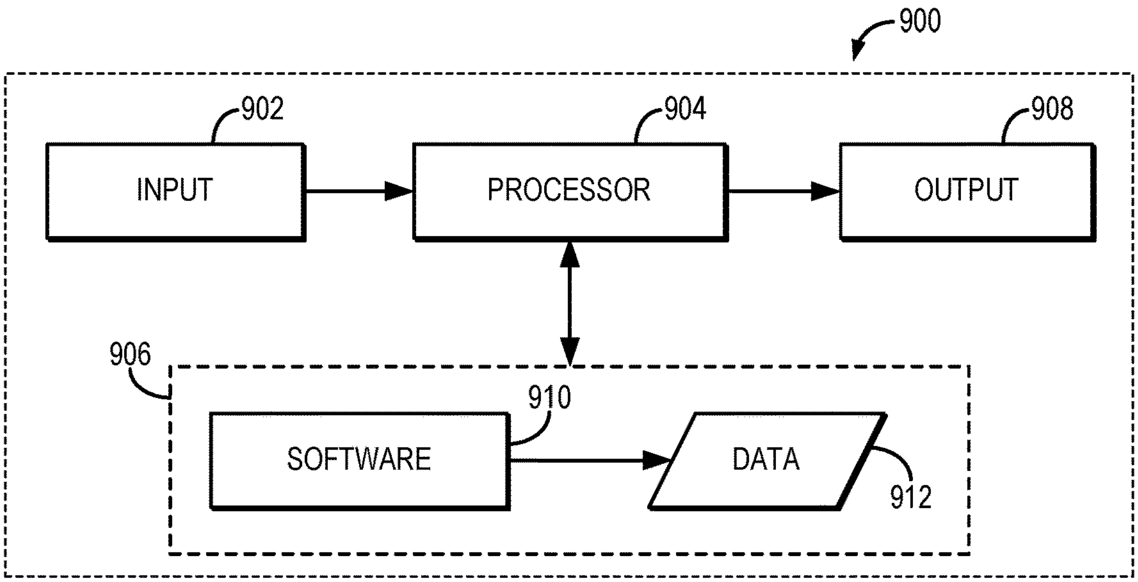

Referring now to FIG. 9, a block diagram of an example of a computer system 900 that can perform the methods described in the present disclosure is shown. The computer system 900 generally includes an input 902, at least one hardware processor 904, a memory 906, and an output 908. Thus, the computer system 900 is generally implemented with a hardware processor 904 and a memory 906.

In some embodiments, the computer system 900 can be a MBI server. The computer system 900 may also be implemented, in some examples, by a workstation, a notebook computer, a tablet device, a mobile device, a multimedia device, a network server, a mainframe, one or more controllers, one or more microcontrollers, or any other general-purpose or application-specific computing device.

The computer system 900 may operate autonomously or semi-autonomously, or may read executable software instructions from the memory 906 or a computer-readable medium (e.g., a hard drive, a CD-ROM, flash memory), or may receive instructions via the input 902 from a user, or any another source logically connected to a computer or device, such as another networked computer or server. Thus, in some embodiments, the computer system 900 can also include any suitable device for reading computer-readable storage media.

In general, the computer system 900 is programmed or otherwise configured to implement the methods and algorithms described in the present disclosure. For instance, the computer system 900 can be programmed to determine the depth of a lesion based upon variation in resolution of a detector with distance.

The input 902 may take any suitable shape or form, as desired, for operation of the computer system 900, including the ability for selecting, entering, or otherwise specifying parameters consistent with performing tasks, processing data, or operating the computer system 900. In some aspects, the input 902 may be configured to receive data, such as data acquired with a MBI system. Such data may be processed as described above to provide data on system resolution and depth of a lesion. In addition, the input 902 may also be configured to receive any other data or information considered useful for using the methods described above.

Among the processing tasks for operating the computer system 900, the one or more hardware processors 904 may also be configured to carry out any number of post-processing steps on data received by way of the input 902. Post-processing may include denoising the MBI data, adjusting gain of the images, segmenting the lesions from the image, and the like.

The memory 906 may contain software 910 and data 912, such as data acquired with, and may be configured for storage and retrieval of processed information, instructions, and data to be processed by the one or more hardware processors 904. In some aspects, the software 910 may contain instructions directed to determining system resolution, determining the distance between detectors, and for determining the depth of a lesion.

In addition, the output 908 may take any shape or form, as desired, and may be configured for displaying lesion depth, in addition to other desired information.

The present disclosure has described one or more preferred embodiments, and it should be appreciated that many equivalents, alternatives, variations, and modifications, aside from those expressly stated, are possible and within the scope of the invention.

The invention claimed is:

1. A molecular breast imaging (MBI) system comprising:

a first detector head operably coupled to the MBI system and comprising:

a first gamma ray detector having a first system resolution;

a second detector head operably coupled to the MBI system and comprising:

a second gamma ray detector having a second system resolution;

a processor in communication with the first detector head and the second detector head, wherein the processor is configured to:

determine the first system resolution of the first gamma ray detector as a function of depth from a facing surface of the first gamma ray detector;

determine the second system resolution of the second gamma ray detector as a function of depth from a facing surface of the second gamma ray detector;

determine a distance between the first detector head and the second detector head; and determine, based on the first system resolution, the second system resolution, and the distance between the first and second detector heads, a depth for a lesion in a breast positioned between the first detector head and the second detector head, wherein the first and second detector heads are moveable relative to each other to provide compression therebetween.

2. The MBI system of claim 1, wherein the processor is further configured to:

receive a first image from the first gamma ray detector;

receive a second image from the second gamma ray detector;

determine a first apparent size for the lesion based on the first image; and determine a second apparent size for the lesion based on the second image.

3. The MBI system of claim 2, wherein the first apparent size and the second apparent size are determined by a full width half maximum (FWHM) of the lesion in the first and second images.

4. The MBI system of claim 1, wherein the processor is further configured to determine the depth for the lesion using a linear model of at least one of the first system resolution or the second system resolution as a function of depth.

5. The MBI system of claim 4, further comprising at least one of a first collimator coupled to the first detector head and the first gamma ray detector, or a second collimator coupled to the second detector head and the second gamma ray detector.

6. The MBI system of claim 5, wherein parameters in the linear model are dependent on at least one of the first collimator or the second collimator.

7. The MBI system of claim 4, wherein parameters of the linear model include slope and intercept.

8. The MBI system of claim 1, wherein the processor is further configured to determine the depth for the lesion according to:

$$D = \frac{FWHM_1^2 - FWHM_2^2 + 2abT + a^2T^2}{2a^2T + 4ab}$$

where $FWHM_1$ represents a full width half maximum of an apparent size for the lesion in detector 1, $FWHM_2$ represents a full width half maximum of an apparent size for the lesion in detector 2, "a" and "b" represent a slope and intercept for a linear model for the first and second system resolutions, T represents the distance between the first detector head and the second detector head, and D represents the depth of the lesion.

9. The MBI system of claim 1, further comprising at least one of a first collimator coupled to the first detector head and the first gamma ray detector, or a second collimator coupled to the second detector head and the second gamma ray detector.

10. A method for determining a depth of a lesion in a breast using a molecular breast imaging (MBI) system comprising:

acquiring a first image of the breast using a first gamma ray detector in a first detector head assembly of the MBI system, and a second image of the breast using a second gamma ray detector in a second detector head assembly of the MBI system;

determining, using a computer system, a first system resolution of the MBI system as a function of depth in the breast relative to the first gamma ray detector;

determining, using the computer system, a second system resolution of the MBI system as a function of depth in the breast relative to the second gamma ray detector;

determining, using the computer system, a distance between the first detector head and the second detector head when the first and second images were acquired; and determining, using the computer system, a depth for the lesion in the breast based on the first system resolution, second system resolution, and the distance between the first and second detector heads.

11. The method of claim 10, further comprising determining a first apparent size for the lesion based on the first image, and determining a second apparent size for the lesion based on the second image.

12. The method of claim 11, wherein the first apparent size and the second apparent size are determined by a full width half maximum (FWHM) of the lesion in the first and second images.

13. The method of claim 10, wherein determining the depth of the lesion includes using a linear model of at least one of the first system resolution or the second system resolution as a function of depth.

14. The method of claim 13, wherein parameters in the linear model are collimator dependent.

15. The method of claim 13, wherein parameters of the linear model include slope and intercept.

16. The method of claim 10, wherein determining the depth of the lesion includes computing the depth, D, as:

$$D = \frac{FWHM_1^2 - FWHM_2^2 + 2abT + a^2T^2}{2a^2T + 4ab}$$

where $FWHM_1$ represents a full width half maximum of an apparent size for the lesion in detector 1, $FWHM_2$ represents a full width half maximum of an apparent size for the lesion in detector 2, "a" and "b" represent a slope and intercept for a linear model for the first and second system resolutions, T represents the distance between the first detector head and the second detector head, and D represents the depth of the lesion.

17. The method of claim 10, wherein the lesion is at least one of a breast lesion or a breast tumor.

* * * * *